(12) United States Patent
Okawa

(10) Patent No.: US 11,045,072 B2
(45) Date of Patent: Jun. 29, 2021

(54) ENDOSCOPE AND METHOD OF OPERATING ENDOSCOPE

(71) Applicant: OLYMPUS CORPORATION, Tokyo (JP)

(72) Inventor: Fumiyuki Okawa, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/939,751

(22) Filed: Jul. 27, 2020

(65) Prior Publication Data

US 2020/0352410 A1 Nov. 12, 2020

Related U.S. Application Data

(63) Continuation of application No. PCT/JP2018/029377, filed on Aug. 6, 2018.

(30) Foreign Application Priority Data

Mar. 6, 2018 (JP) .............................. JP2018-040158

(51) Int. Cl.
*A61B 1/00* (2006.01)
*H04N 5/00* (2011.01)
(Continued)

(52) U.S. Cl.
CPC ........ *A61B 1/0002* (2013.01); *A61B 1/00006* (2013.01); *A61B 1/00009* (2013.01);
(Continued)

(58) Field of Classification Search
CPC ......... H04N 2005/2255; H04N 5/2253; G02B 23/24; A61B 1/00006; A61B 1/00059;
(Continued)

(56) References Cited

U.S. PATENT DOCUMENTS 6,436,032 B1 * 8/2002 Eto .................... A61B 1/00059
600/117
6,638,212 B1 * 10/2003 Oshima ................ A61B 1/0002
348/72

(Continued)

FOREIGN PATENT DOCUMENTS

JP 2015-104616 A 6/2015
JP 2016-116750 A 6/2016

(Continued)

OTHER PUBLICATIONS

International Search Report dated Oct. 30, 2018 issued in PCT/JP2018/029377.

*Primary Examiner* — Zhihan Zhou
(74) *Attorney, Agent, or Firm* — Scully, Scott, Murphy & Presser, P.C.

(57) ABSTRACT

An endoscope includes an image sensor and a first memory, which is a nonvolatile memory, storing first information disposed in a distal end portion, and includes a controller and a second memory configured to back up the first information disposed on a proximal end side relative to the distal end portion. The controller reads out the first information stored in the first memory and stores the read first information as a backup in the second memory when the controller is started when supplied with power, and reads out the first information stored in the second memory and transmits the read first information to a video processor when the controller receives a request from the video processor.

13 Claims, 7 Drawing Sheets

(51) Int. Cl.
*A61B 1/05* (2006.01)
*H04N 5/225* (2006.01)

(52) U.S. Cl.
CPC ............ *A61B 1/00114* (2013.01); *A61B 1/05* (2013.01); *H04N 5/2253* (2013.01); *H04N 2005/2255* (2013.01)

(58) Field of Classification Search
CPC ....... A61B 1/05; A61B 1/045; A61B 1/00009; A61B 1/00114; A61B 1/00057; A61B 1/0002
See application file for complete search history.

(56) References Cited

U.S. PATENT DOCUMENTS

| | | | | |
|---|---|---|---|---|
| 2006/0174133 | A1* | 8/2006 | Obata | G06F 21/31 713/182 |
| 2008/0074492 | A1* | 3/2008 | Iwasaki | A61B 1/045 348/68 |
| 2008/0183981 | A1* | 7/2008 | Tannai | H04N 5/232 711/154 |
| 2012/0200683 | A1* | 8/2012 | Oshima | G06T 11/60 348/65 |
| 2017/0280037 | A1* | 9/2017 | Sakai | A61B 1/0638 |

FOREIGN PATENT DOCUMENTS

| | | |
|---|---|---|
| JP | 2016-209113 A | 12/2016 |
| JP | 2017-225700 A | 12/2017 |

* cited by examiner

ENDOSCOPE AND METHOD OF OPERATING ENDOSCOPE

CROSS REFERENCE TO RELATED APPLICATION

This application is a continuation application of PCT/JP2018/029377 filed on Aug. 6, 2018 and claims benefit of Japanese Application No. 2018-040158 filed in Japan on Mar. 6, 2018, the entire contents of which are incorporated herein by this reference.

BACKGROUND OF THE INVENTION

1. Field of the Invention

The present invention relates to an endoscope and a method of operating the endoscope, and more particularly to an endoscope including a solid-state image pickup device and a method of operating the endoscope.

2. Description of the Related Art

An endoscope system including an endoscope configured to pick up an image of an object in a subject, an image processing apparatus configured to generate an observation image of the object obtained by image pickup by the endoscope, and the like has been widely used in a medical field, an industrial field, and the like.

As the endoscope in the endoscope system, an endoscope adopting a CMOS image sensor, for example, as a solid-state image pickup device and configured to transmit an image pickup signal to be outputted from the CMOS image sensor to an image processing apparatus in a succeeding stage has been widely known. The above-described CMOS image sensor is generally supplied with predetermined power, and is driven by a predetermined control signal.

In recent years, in an endoscope of this type, an example in which a nonvolatile memory storing various pieces of information about the endoscope itself is mounted on a connector substrate disposed on a proximal end side of an insertion section has been known (Japanese Patent. Application Laid-Open Publication No. 2016-116750). The nonvolatile memory stores individual variation data of a solid-state image pickup device, a name of an endoscope used in an endoscope system, white balance data for correcting a variation of the entire endoscope system, and the like.

In the endoscope system including the endoscope as described above, when an image pickup unit including the solid-state image pickup device has failed, for example, the image pickup unit (including the solid-state image pickup device) to be mounted on the endoscope may be required to be replaced. In this case, as the image pickup unit is replaced, the solid-state image pickup device to be mounted on the endoscope is also changed.

SUMMARY OF THE INVENTION

An endoscope according to an aspect of the present invention includes an image sensor disposed in a distal end portion in an insertion section to be inserted into a subject, a first memory, which is a nonvolatile memory, disposed in the distal end portion and storing first information, a controller disposed on a proximal end side relative to the distal end portion, electrically connected to the image sensor and the first memory, and communicable with the image sensor and the first memory, and a second memory disposed on a proximal end side relative to the distal end portion, storing second information, and communicable with the controller, in which the controller reads out the first information stored in the first memory and stores the first information as backup information in the second memory separately from the second information or as a part of the second information when the controller is started when supplied with power, and reads out the first information stored in the second memory and transmits the read first information to a predetermined circuit when the controller receives a request from the circuit.

A method of operating an endoscope according to an aspect of the present invention is a method of operating an endoscope including an image sensor disposed in a distal end portion in an insertion section to be inserted into a subject, a first memory, which is a nonvolatile memory, disposed in the distal end portion and storing first information, a controller disposed on a proximal end side relative to the distal end portion, electrically connected to the image sensor and the first memory, and communicable with the image sensor and the first memory, and a second memory disposed on a proximal end side relative to the distal end portion, storing second information, and communicable with the controller, the method including the controller reading out the first information stored in the first memory when the controller is started when supplied with power, the controller storing the read first information as backup information in the second memory separately from the second information or as a pail of the second information, and the controller reading out the first information stored in the second memory and transmitting the read first information to a predetermined circuit when the controller receives a request from the circuit.

DETAILED DESCRIPTION OF THE PREFERRED EMBODIMENTS

Embodiments of the present invention will be described below with reference to the drawings.

First Embodiment

Figure 1:
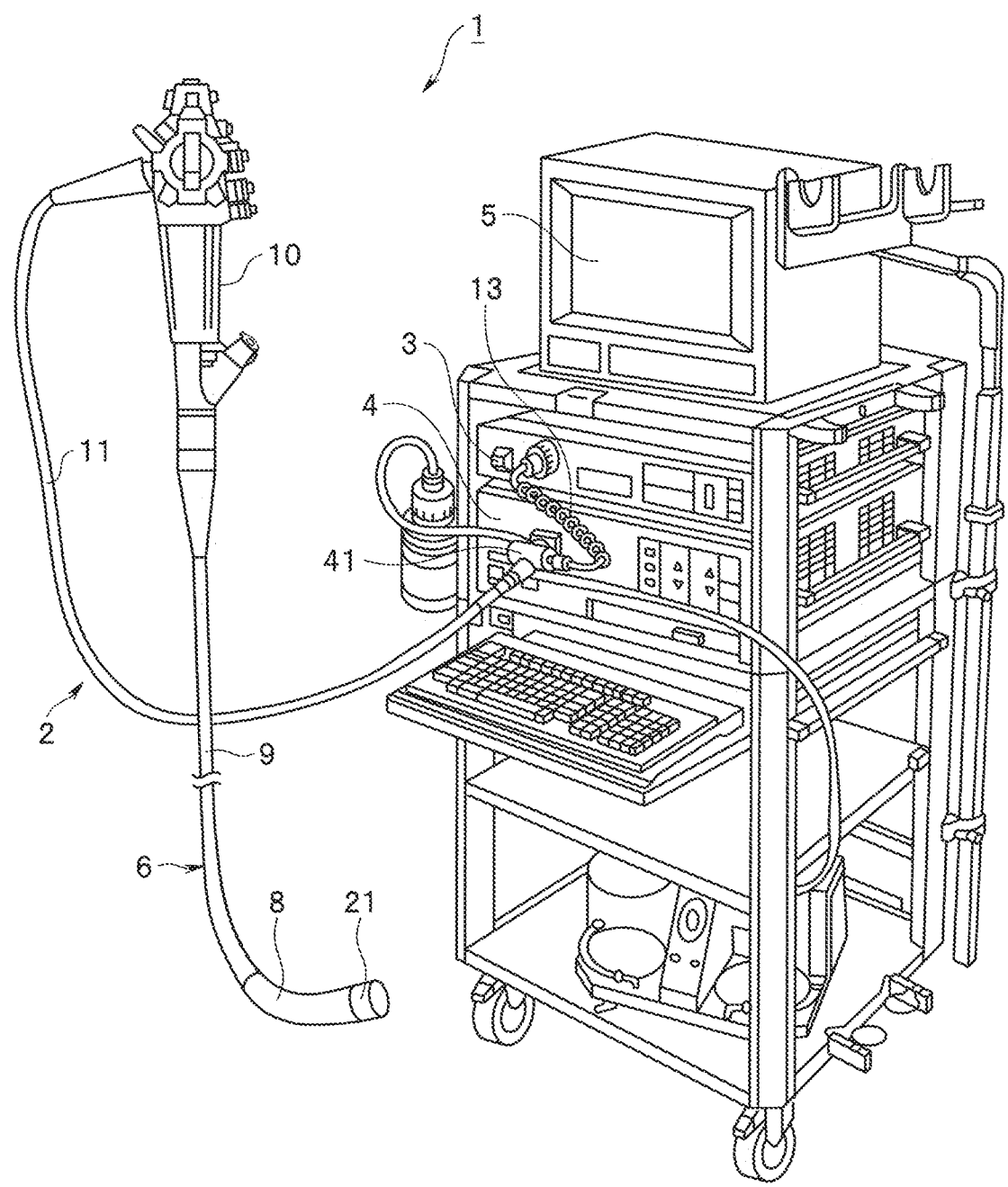
FIG. 1 is an external view illustrating a configuration of an endoscope system including an endoscope according to a first embodiment of the present invention.
Figure 2:
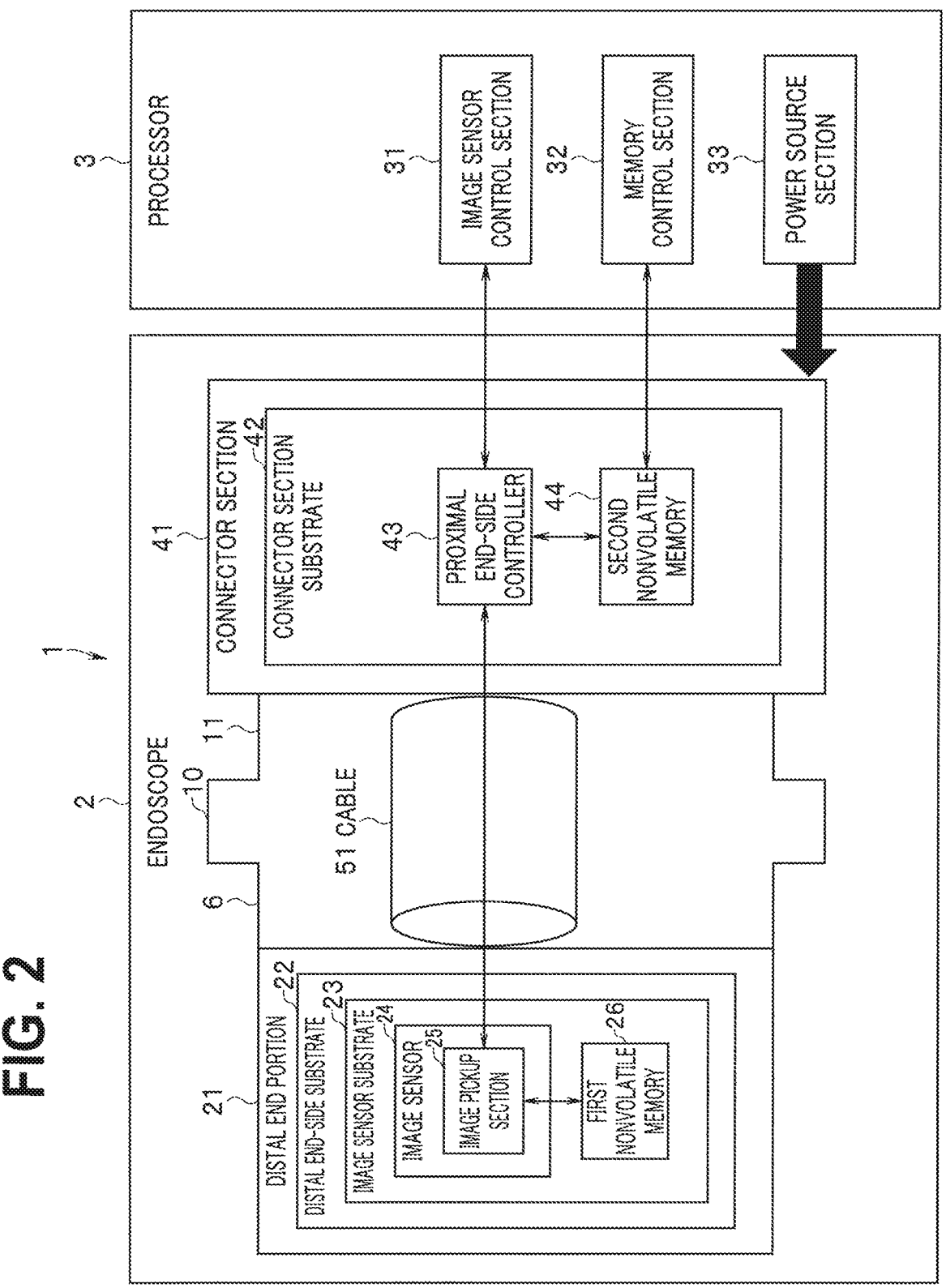
FIG. 2 is a diagram illustrating the configuration of the endoscope system including the endoscope according to the first embodiment.

FIG. 1 is an external view illustrating a configuration of an endoscope system including an endoscope according to a first embodiment of the present invention, and FIG. 2 is a diagram illustrating an electrical configuration of the endoscope system including, the endoscope according to the first embodiment.

Note that in the present embodiment, an endoscope including a solid-state image pickup device (CMOS image sensor) and configured to pick up an image of an object in a subject will be described as an example of the endoscope.

As illustrated in FIGS. 1 and 2, an endoscope system 1 including an endoscope according to the first embodiment includes an endoscope 2 according to the present embodiment configured to observe and pick up an image of a subject and output an image pickup signal, a video processor 3 connected to the endoscope 2 and configured to receive the image pickup signal and subject the received image pickup signal to predetermined image processing, a light source device 4 configured to supply illumination light for illuminating the subject, and a monitor 5 configured to display the image pickup signal or the like.

As illustrated in FIG. 1, the endoscope 2 is configured to include an endoscope operation section 10 disposed on a proximal end side of the insertion section 6 and configured to perform an operation while being grasped by an operator, and a universal code 11 having one end provided to extend from a side of the endoscope operation section 10 in addition to an elongated insertion section 6 to be inserted into a body cavity of the subject, for example.

<Distal End Portion 21>

The insertion section 6 is configured to include, in addition to a rigid distal end portion 21 provided on a distal end side, a bendable bending portion 8 provided at a rear end of the distal end portion 21 and a flexible tube portion 9 being long and having flexibility provided at a rear end of the bending portion 8.

An objective optical system (not illustrated) including a lens configured to receive light of an object image and an image sensor 24 (see FIG. 2) disposed on an image formation surface in the objective optical system are disposed in the distal end portion 21.

<First Substrate: Distal End-Side Substrate 22>

A distal end-side substrate 22 including a circuit board such as an image sensor substrate 23 is disposed, as illustrated in FIG. 2, in the distal end portion 21. In the present embodiment, the image sensor 24, described above, and a first nonvolatile memory 26 are mounted on the image sensor substrate 23. Note that in the present embodiment, the distal end-side substrate 22 is referred to as a first substrate.

<Image Sensor 24>

The image sensor 24 is a solid-state image pickup device configured by a CMOS image sensor in the present embodiment. The image sensor 24 forms a predetermined image pickup section 2S, photoelectrically converts an object light of which has been received to generate a predetermined image pickup signal, and outputs the generated image pickup signal toward a succeeding stage (via a cable 51).

<First Nonvolatile Memory 26>

The first nonvolatile memory 26 previously stores specific information linked to the image sensor 24, for example, characteristic variation information and information not updated (sensitivity information, pixel defect information, a serial number of the image sensor 24, etc.). Note that in the present embodiment, the pieces of information are each referred to as first information.

In the present embodiment, both the image sensor 24 and the first nonvolatile memory 26 are mounted on the image sensor substrate 23, and the first information to be stored in the first nonvolatile memory 26 is always operated together with the image sensor 24.

As illustrated in FIGS. 1 and 2, the endoscope 2 is extended from the image sensor 24, and includes the cable 51 disposed from the image sensor 24 to a connector section 41 via the insertion section 6, the operation section 10, and the universal code 11.

<Connector Section 41>

On the other hand, the connector section 41 is provided on a proximal end side of the universal code 11, and the connector section 41 is connected to the above-described light source device 4, as illustrated in FIG. 1. In other words, a pipe sleeve (not illustrated) as a connection end portion of a fluid channel protruding from a distal end of the connector section 41 and a light guide pipe sleeve (not illustrated) as a supply end portion of illumination light are detachably connected to the light source device 4.

Further, one end of a connection cable 13 is connected to an electrical contact portion provided on a side surface of the connector section 41. The connection cable 13 is internally provided with a signal line configured to transmit an image pickup signal from the image sensor 24 in the endoscope 2, for example, which has been transmitted via the cable 51, and the other end of the connection cable 13 is connected to the video processor 3.

<Second Substrate: Connector Section Substrate 42>

Referring to FIG. 2 again, in the connector section 41, a connector section substrate 42 configured to mount various electrical circuits, for example, an FPGA and a power regulator section is disposed in addition to a proximal end-side controller 43 configured to control driving of the image sensor 24 and a second nonvolatile memory 44 configured to store predetermined information about the endoscope 2.

<Proximal End-Side Controller 43>

The proximal end-side controller 43 is configured by a so-called FPGA (field programmable gate array) and performs various types of timing adjustments related to the image sensor 24 under control of an image sensor control section 31 in the video processor 3. The proximal end-side controller 43 receives the image pickup signal from the image sensor 24 and subjects the received image pickup signal to predetermined processing, and then transmits the image pickup signal to the image sensor control section 31 as an image processing section in the video processor 3.

The proximal end-side controller 43 is electrically connected to the image sensor 24 and the first nonvolatile memory 26 disposed in the first substrate (the distal end-side substrate 22) and is configured to be communicable with the image sensor 24 and the first nonvolatile memory 26.

Further, the proximal end-side controller 43 operates when supplied with power from a power source section 33 in the video processor 3 in the present embodiment.

Note that the proximal end-side controller 43 reads out the first information stored in the second nonvolatile memory 44 described below and transmits the read first information to the video processor 3 when the proximal end-side controller 43 receives a request from a predetermined circuit in an external device or the like, for example, a memory control section 32 in the video processor 3.

<Second Nonvolatile Memory 44>

The second nonvolatile memory 44 is communicably connected to the proximal end-side controller 43. In the present embodiment, as the second nonvolatile memory 44, a second nonvolatile memory of a type having a larger memory capacity than a memory capacity of the first nonvolatile memory 26 disposed in the distal end-side substrate 22 is adopted.

The second nonvolatile memory 44 stores information such as image processing information (a white balance, etc.) for correcting a variation of the entire endoscope system in addition to specific information about the endoscope 2, for example, a so-called scope ID being, stored. Note that in the present embodiment, the information are each referred to as second information.

When the proximal end-side controller 43 is started when supplied with power from the video processor 3, the second nonvolatile memory 44 in the present embodiment stores the first information stored in the first nonvolatile memory 26 as backup information in the second nonvolatile memory 44 separately from the second information or as a part of the second information under control of the proximal end-side controller 43.

The first information stored as backup information in the second nonvolatile memory 44 is read out by the proximal end-side controller 43 when the proximal end-side controller 43 receives a request from the memory control section 32 in the video processor 3, for example, and is transmitted to the video processor 3 under control of the proximal end-side controller 43.

On the other hand, the video processor 3 to which the endoscope 2 in the present embodiment is connected includes the image sensor control section 31, the memory control section 32, and the power source section 33, as illustrated in FIG. 2.

The image sensor control section 31 is connected to the proximal end-side controller 43 disposed in the connector section 41 in the endoscope 2, and transmits various signals for controlling driving of the image sensor 24 to the proximal end-side controller 43 and subjects the image pickup signal from the image sensor 24 to predetermined image processing.

The memory control section 32 is connected to the proximal end-side controller 43 and the second nonvolatile memory 44, and controls the proximal end-side controller 43 to read out the first information stored in the second nonvolatile memory 44.

The power source section 33 has a function as a power source of each of circuit sections in the video processor 3, and has a function as a power source of each of circuit sections (a circuit section such as the proximal end-side controller 43 in the connector section 41 and a circuit section such as the image sensor 24 in the distal end portion 21) in the endoscope 2.

The circuit sections such as the proximal end-side controller 43 and the image sensor 24 in the endoscope 2 are started when supplied with power from the power source section 33.

Note that the video processor 3 and the endoscope 2 may be respectively provided with regulators, and the regulator that has been supplied with power from the power source section 33 may generate a power source voltage related to each of the circuit sections in the video processor 3 or each of the circuit sections in the endoscope 2.

Function of Present Embodiment

Next, a function of the endoscope according to the first embodiment will be described with reference to FIG. 3.

Figure 3:
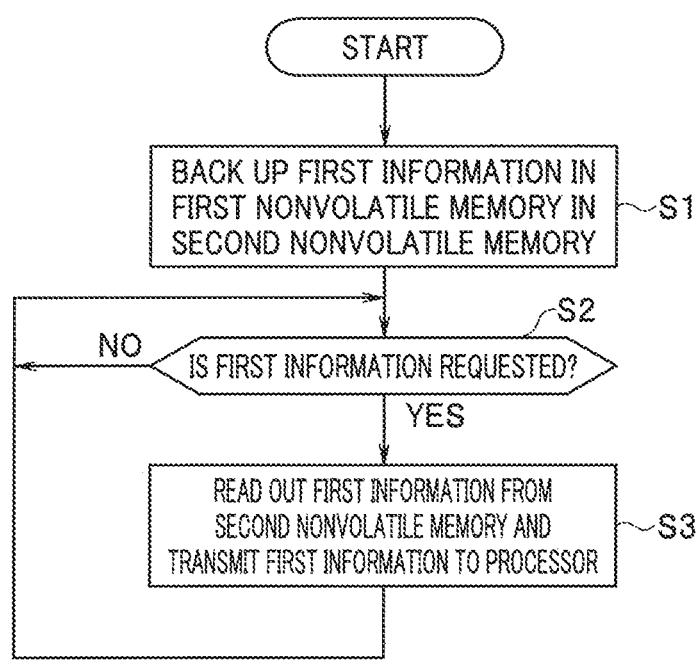
FIG. 3 is a flowchart illustrating a procedure in replacing a solid-state image pickup device in the endoscope according to the first embodiment.

FIG. 3 is a flowchart illustrating a procedure in replacing the solid-state image pickup device in the endoscope according to the first embodiment.

As illustrated in FIG. 3, in the present embodiment, first information stored in the first nonvolatile memory 26 disposed in the distal end-side substrate 22 is stored as backup information in the second nonvolatile memory 44 disposed in the connector section substrate 42 under control of the proximal end-side controller 43 disposed in the connector section substrate 42 in the endoscope 2 (step S1).

More specifically, when the proximal end-side controller 43 is started when supplied with power from the video processor 3, the proximal end-side controller 43 reads out the first information stored in the first nonvolatile memory 26, and stores the first information as backup information in the second nonvolatile memory 44 separately from the second information or as a part of the second information (step S1).

Then, when the proximal end-side controller 43 receives a request to provide first information from the memory control section 32 in the video processor 3 (step S2), the proximal end-side controller 43 reads out the first information stored as backup information in the second nonvolatile memory 44 and transmits the read first information to the video processor 3 (step S3).

Effect of Present Embodiment

As described above, in the endoscope according to the first embodiment, the connector section substrate 42 in the connector section 41 in the endoscope 2 is provided with the second nonvolatile memory 44 storing specific information (second information) about the endoscope 2, while the distal end-side substrate 22 in the distal end portion 21 in the endoscope 2 is provided with the image sensor substrate 23 in which the first nonvolatile memory 26 storing only specific information (first information) linked to the image sensor 24, together with the image sensor 24, is disposed.

When the proximal end-side controller 43 in the connector section 41 is stalled when supplied with power from the video processor 3, the proximal end-side controller 43 stores the first information stored in the first nonvolatile memory 26 as backup information in the second nonvolatile memory 44 separately from the second information or as a part of the second information, and transmits the first information backup-stored in not the first nonvolatile memory 26 but the second nonvolatile memory 44 to the video processor 3 when first information is requested from the video processor 3.

Accordingly, the image sensor substrate 23 in which the first nonvolatile memory 26 storing only specific information (first information) linked to the image sensor 24, together with the image sensor 24, is disposed is provided in the distal end portion 21 in the endoscope 2, and the first information is backed up in the second nonvolatile memory 44 disposed in the connector section substrate 42 on a proximal end side of the endoscope 2 always (always when the endoscope 2 is started). Thus, even in the video processor 3, it is ensured that the first information as the specific information about the image sensor 24 is accurately acquired at a desired timing, while it suffices to replace the image sensor substrate 23 in the distal end portion 21 even when the image pickup unit (the image sensor 24) is repaired so that the repair can be performed in a short time period.

In the endoscope 2 according to the present embodiment, every time the image sensor 24 is replaced, since the specific information linked to the image sensor 24 need not be written into the memory on the side of the connector section 41, a repair time period can be shortened.

In other words, a new image sensor 24 and a new first nonvolatile memory 26 storing first information about the image sensor 24 are mounted on a new image sensor substrate 23 obtained by replacement. Thus, since specific information about the image sensor 24 need not be written again into the memory on the side of the connector section 41 during repair, a repair time period can be shortened.

In the endoscope 2 according to the present embodiment, the first information as the specific information about the image sensor 24 is acquired only at a timing requested from the video processor 3 (in other words, the first information is acquired only at a desired timing from the external device). Thus, the first information can be acquired while avoiding a timing at which disturbance noise due to electrocautery or the like occurs, and an effect of such disturbance noise can be reduced, for example.

Second Embodiment

Then, a second embodiment of the present invention will be described.

Figure 4:
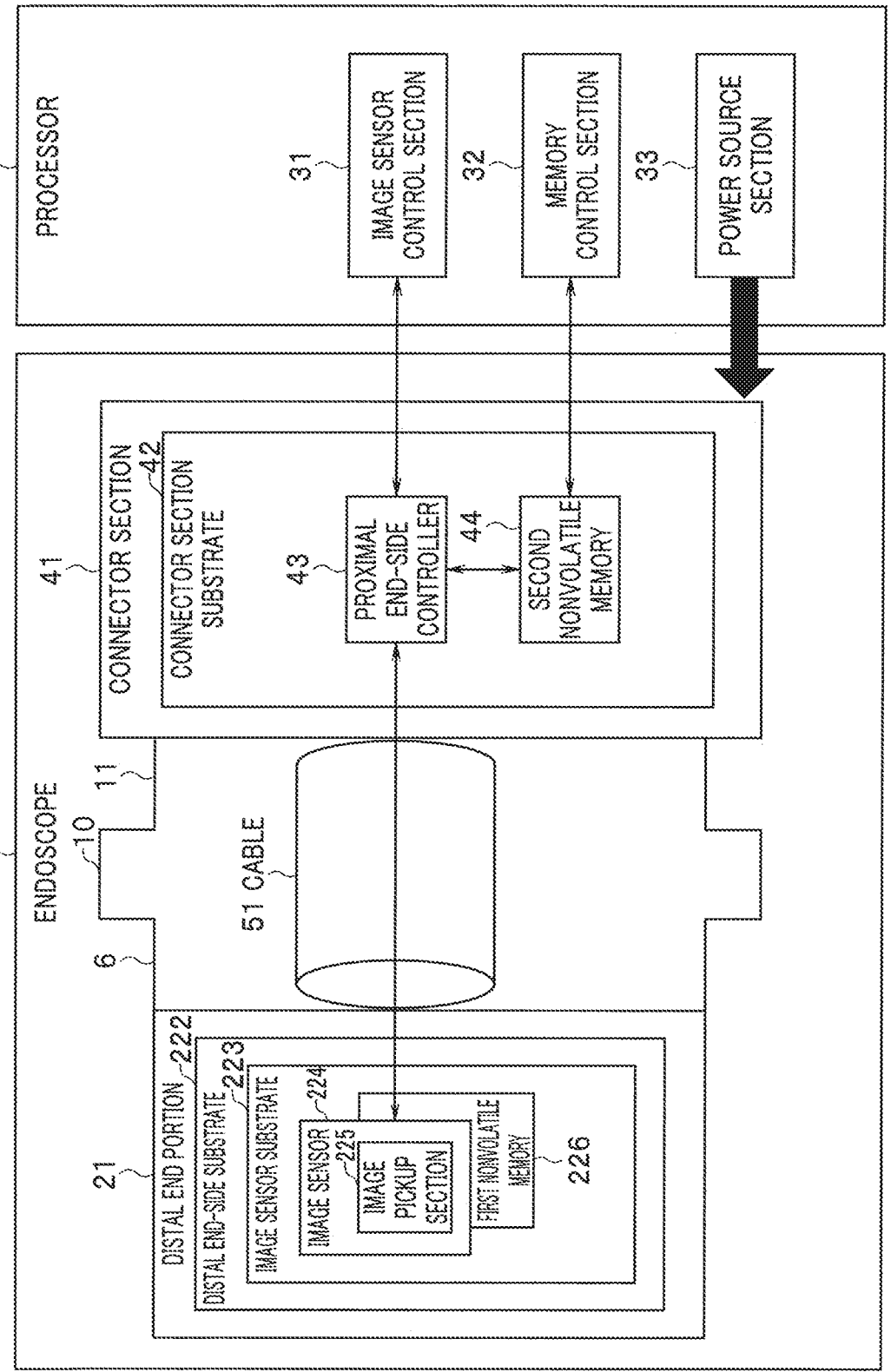
FIG. 4 is a diagram illustrating a configuration of an endoscope system including an endoscope according to a second embodiment of the present invention.

FIG. 4 is a diagram illustrating a configuration of an endoscope system including an endoscope according to the second embodiment of the present invention.

Although an endoscope system 201 including an endoscope 202 according to the second embodiment is similar to the endoscope system according to the first embodiment in a basic configuration, the endoscope 202 according to the second embodiment differs from the endoscope 2 according to the first embodiment in a method of mounting a first nonvolatile memory on an image sensor substrate.

Therefore, only a difference from the first embodiment is described, and description of common parts is omitted.

In the endoscope according to the first embodiment described above, the image sensor 24 including the image pickup section 25 is mounted on the image sensor substrate 23 disposed on the distal end-side substrate 22 as a first substrate, and the first nonvolatile memory 26 is mounted as an IC package separate from the image sensor 24 on the image sensor substrate 23.

On the other hand, although the endoscope 202 according to the second embodiment is similar to the endoscope according to the first embodiment in that an image sensor 224 including an image pickup section 225 is mounted on an image sensor substrate 223 disposed on a distal end-side substrate 222 as a first substrate, as illustrated in FIG. 4, a first nonvolatile memory 226 is stacked and mounted on the image sensor 224 on the image sensor substrate 223 in the endoscope 202 according to the second embodiment.

Other components and a function and effect are similar to the components and the function and effect in the first embodiment. For example, even when an image pickup unit (the image sensor 224) is repaired, it suffices to replace the image sensor substrate 223 in the distal end portion 21 so that the repair can be performed in a short time period.

Third Embodiment

Next, a third embodiment of the present invention will be described.

Figure 5:
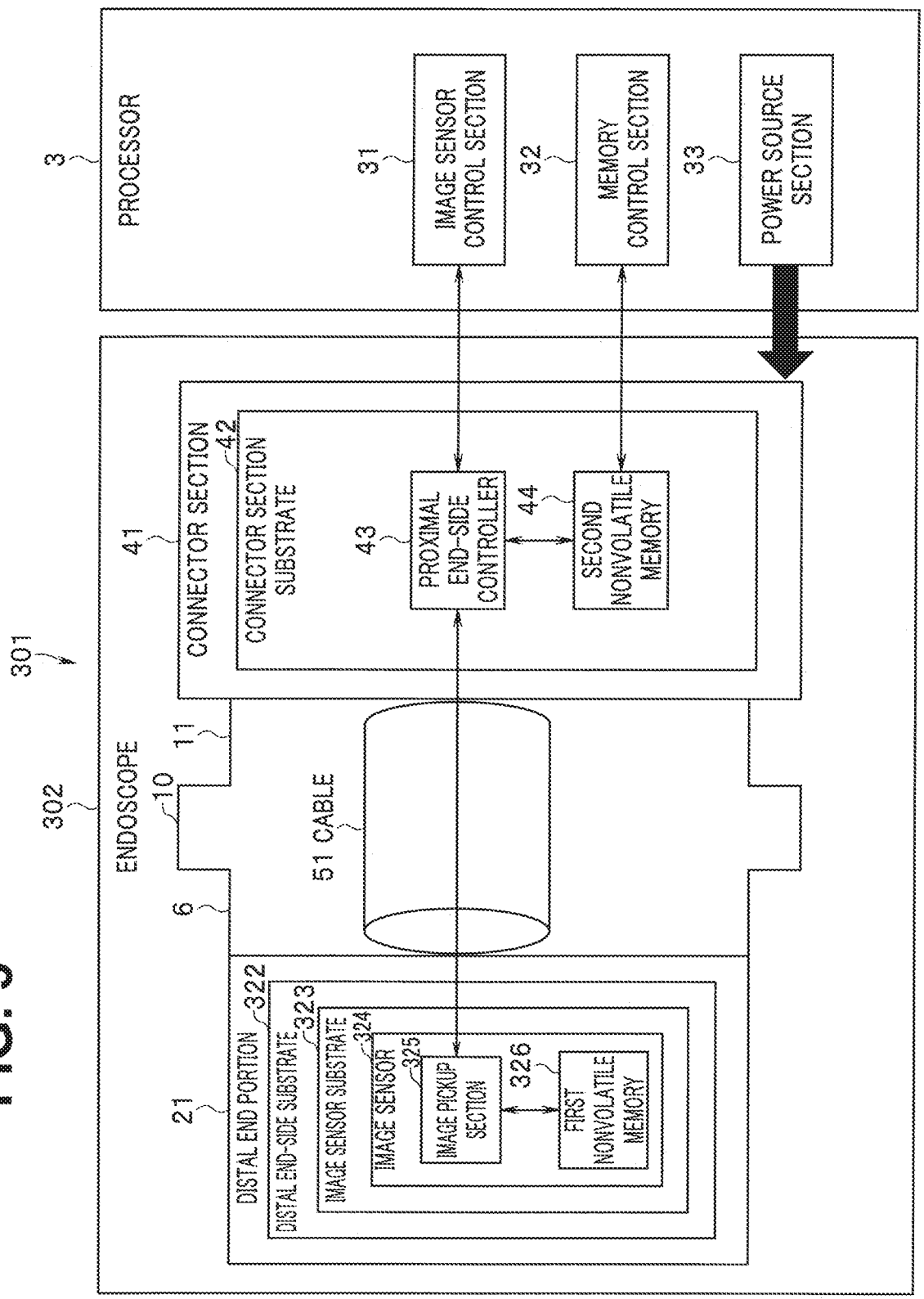
FIG. 5 is a diagram illustrating a configuration of an endoscope system including an endoscope according to a third embodiment of the present invention.

FIG. 5 is a diagram illustrating a configuration of an endoscope system including an endoscope according to the third embodiment of the present invention.

Although an endoscope system 301 including an endoscope 302 according to the third embodiment is similar to the endoscope system according to the first embodiment in a basic configuration, the endoscope 302 according to the third embodiment differs from the endoscope 2 according to the first embodiment in a method of mounting a first nonvolatile memory on an image sensor substrate.

Therefore, only a difference from the first embodiment is described, and description of common parts is omitted.

Although the endoscope 302 according to the third embodiment is similar to the endoscope according to the first embodiment in that an image sensor 324 including an image pickup section 325 is mounted on an image sensor substrate 323 disposed on a distal end-side substrate 322 as a first substrate, as illustrated in FIG. 5, a first nonvolatile memory 326 is provided in the image sensor 324 on the image sensor substrate 323 in the endoscope 302 according to the third embodiment.

Other components and a function and effect are similar to the components and the function and effect in the first embodiment. For example, even when an image pickup unit (the image sensor 324) is repaired, it suffices to replace the image sensor substrate 323 in the distal end portion 21 so that the repair can be performed in a short time period.

Fourth Embodiment

Next, a fourth embodiment of the present invention will be described.

Figure 6:
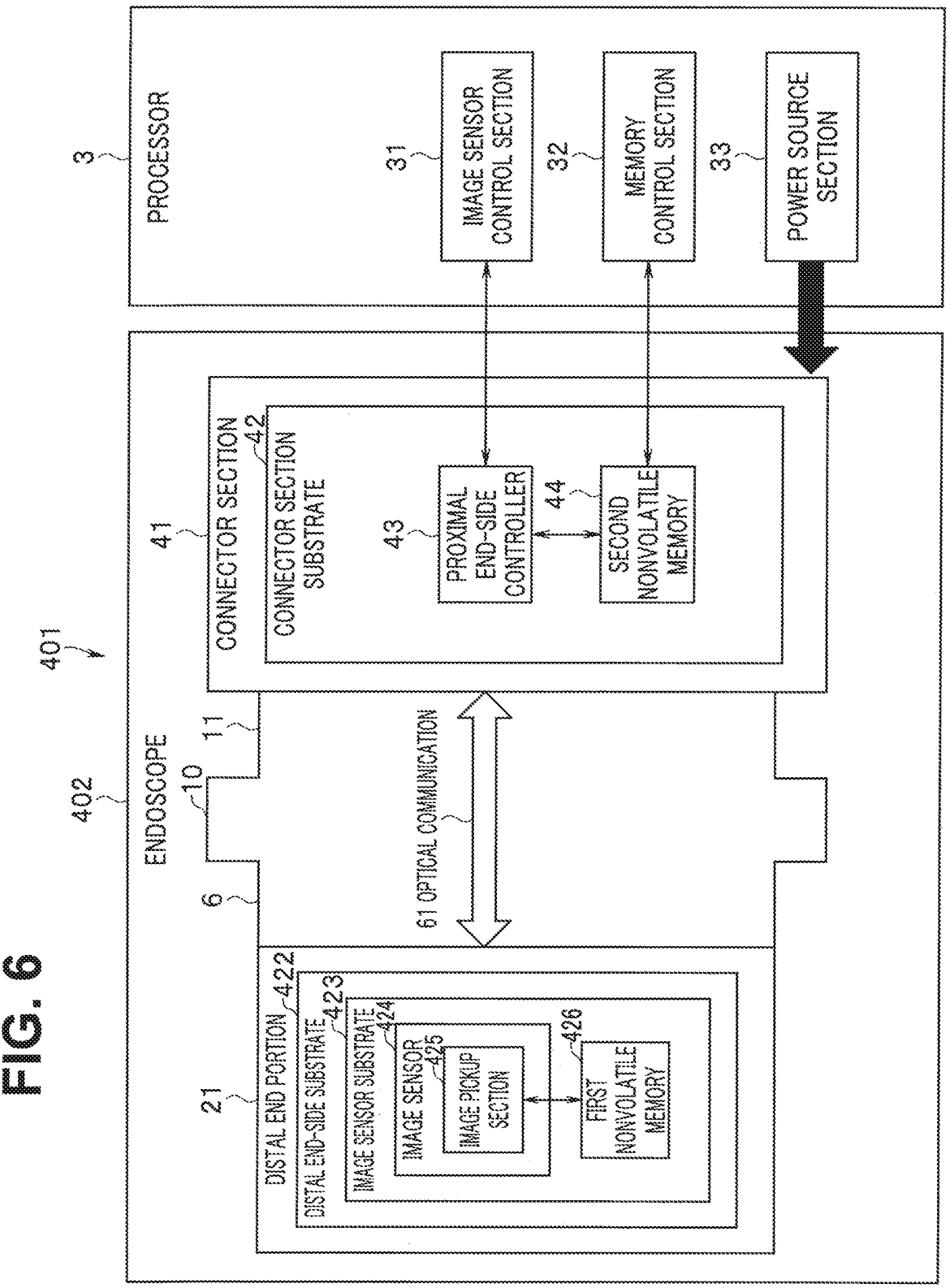
FIG. 6 is a diagram illustrating a configuration of an endoscope system including an endoscope according to a fourth embodiment of the present invention.

FIG. 6 is a diagram illustrating a configuration of an endoscope system including an endoscope according to the fourth embodiment of the present invention.

Although an endoscope system 401 including an endoscope 402 according to the fourth embodiment is similar to the endoscope system according to the first embodiment in a basic configuration, the endoscope 402 according to the fourth embodiment differs from the endoscope 2 according to the first embodiment in that optical communication 61 is adopted instead of the cable 51 configured to transmit various types of signals.

Therefore, only a difference from the first embodiment is described, and description of common parts is omitted.

Although in the endoscope 2 according to the first embodiment described above, the distal end-side substrate 22 and the connector section substrate 42 are connected to each other via the cable 51, a distal end-side substrate 422 and a connector section substrate 42 are connected to each other via the optical communication 61 in the endoscope 402 according to the fourth embodiment.

Note that the endoscope 402 according to the fourth embodiment also includes the distal end-side substrate 422 having a similar configuration to the configuration of the distal end-side substrate 22 in the first embodiment, as illustrated in FIG. 6. In other words, in the endoscope 402, an image sensor 424 including an image pickup section 425 is mounted on an image sensor substrate 423 in a distal end portion 21, and a first nonvolatile memory 426 is mounted as an IC package separate from the image sensor 424 on the image sensor substrate 423.

Other components and a function and effect are similar to the components and the function and effect in the first embodiment. For example, even when an image pickup unit (the image sensor 424) is repaired, it suffices to replace the image sensor substrate 423 in the distal end portion 21 so that the repair can be performed in a short time period.

Fifth Embodiment

Next, a fifth embodiment of the present invention will be described.

Figure 7:
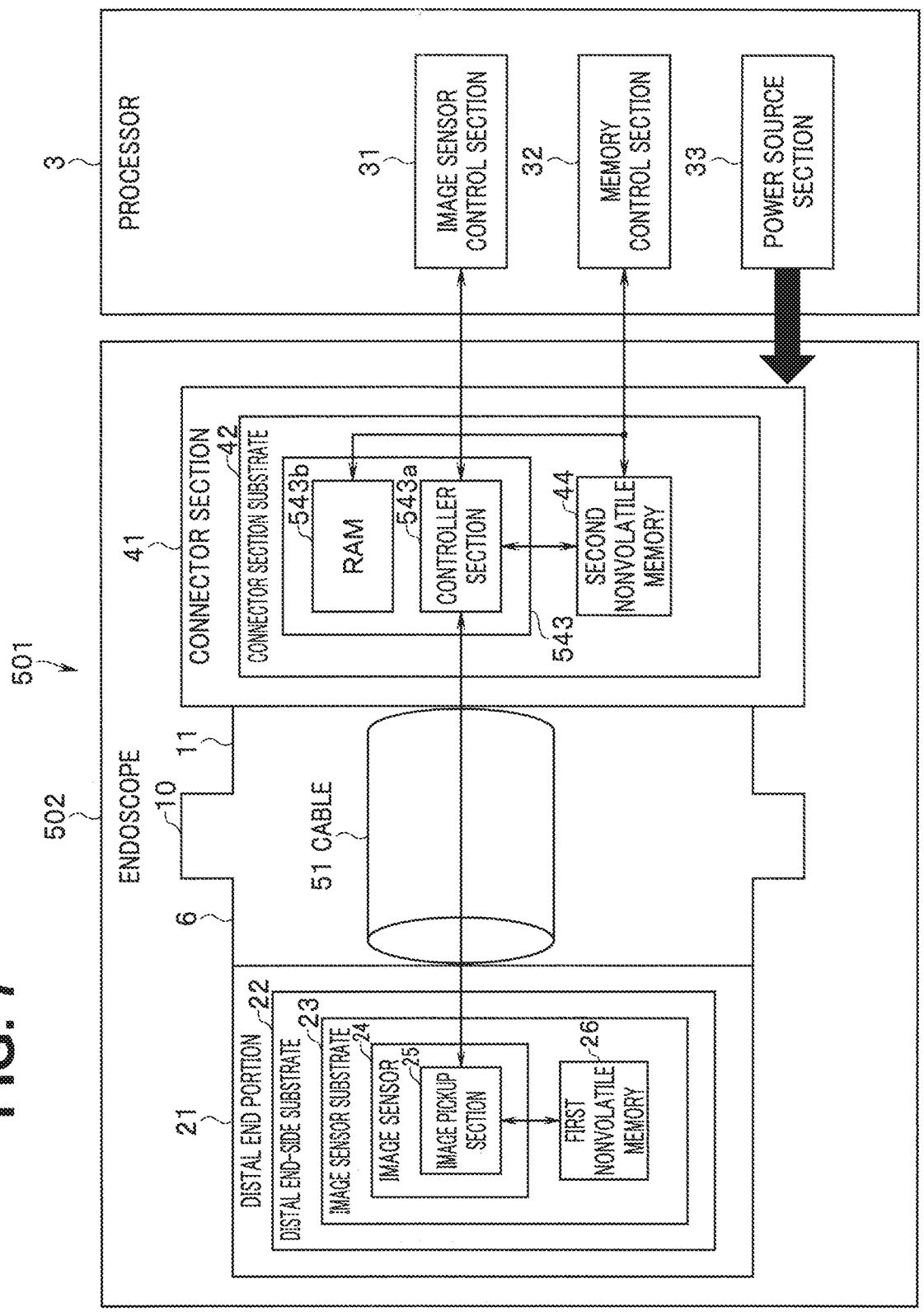
FIG. 7 is a diagram illustrating a configuration of an endoscope system including an endoscope according to a fifth embodiment of the present invention.

FIG. 7 is a diagram illustrating a configuration of an endoscope system including an endoscope according to the fifth embodiment of the present invention.

Although an endoscope system 501 including an endoscope 502 according to the fifth embodiment is similar to the endoscope system according to the first embodiment in a basic configuration, the endoscope 502 according to the fifth embodiment differs from the endoscope 2 according to the first embodiment in a configuration in a proximal end-side controller 543 in a connector section 41.

Therefore, only a difference from the first embodiment is described, and description of common parts is omitted.

In the endoscope 502 according to the fifth embodiment, the proximal end-side controller 543 is disposed on a connector section substrate 42, as illustrated in FIG. 7.

In the fifth embodiment, in the proximal end-side controller 543, a controller section 543a, which is configured by a so-called FPGA (field programmable gate array) and is configured to perform various types of timing adjustments related to an image sensor 24 under control of an image sensor control section 31 in a video processor 3, is also formed in the fifth embodiment.

The controller section 543a in the proximal end-side controller 543 receives an image pickup signal from the image sensor 24 and subjects the received image pickup signal to predetermined processing, and then transmits the image pickup signal to an image sensor control section 31 as an image processing section in the video processor 3.

Further, the controller section 543a in the proximal end-side controller 543 is electrically connected to the image sensor 24 and a first nonvolatile memory 26 disposed in a first substrate (distal end-side substrate 22), and is configured to be communicable with the image sensor 24 and the first nonvolatile memory 26.

Further, the proximal end-side controller 543 also operates when supplied with power from a power source section 33 in the video processor 3 in the fifth embodiment.

On the other hand, in the proximal end-side controller 543 in the fifth embodiment, a RAM (random access memory) 543b connected to a memory control section 32 in an external device, for example, the video processor 3 is formed.

The controller section 543a reads out the first information stored in a second nonvolatile memory 44, like in the first embodiment, and transmits the read first information to the video processor 3 via the RAM 543b when the RAM 543b receives a request from the video processor 3.

At this time, data accessed from the video processor 3 is stored in the RAM 543b. When the video processor 3 accesses the same data again, the controller section 543a does not read the data from the second nonvolatile memory 44 but reads out the data already stored in the RAM 543b, and transmits the read data to the video processor 3. The RAM 543b functions as a so-called cache memory, and thus can shorten, when accessing the same data a plurality of times, an access time period (data acquisition time period) for second and subsequent accesses.

Other components and a function and effect are similar to the components and the function and effect in the first embodiment. For example, even when an image pickup unit (the image sensor 24) is repaired, it suffices to replace an image sensor substrate 23 in a distal end portion 21 so that the repair can be performed in a short time period.

Although in each of the above-described embodiments, the proximal end-side controller 43 and the second nonvolatile memory 44 disposed in the connector section substrate 42 as a second substrate are disposed in the connector section 41, the present invention is not limited to this. The proximal end-side controller 43 and the second nonvolatile memory 44 may be disposed in the operation section 10.

In other words, the proximal end-side controller 43 and the second nonvolatile memory 44 may be disposed in not only the connector section 41 on a proximal end side of a signal line extending from the distal end-side substrate 22 but also the operation section 10 on the same proximal end side of the signal line.

According to the present invention, an endoscope capable of shortening an operation time period when the solid-state image pickup device mounted on the endoscope is replaced and a method of operating the endoscope.

Although in each of the above-described embodiments, a configuration of the endoscope system including the endoscope is taken as an example of the present invention, the present invention is not limited to this. The present invention is also applicable to another image pickup system having an image processing function.

Further, the present invention is not limited to the above-described embodiments, but various changes, alterations, and the like are possible without departing from the gist of the present invention. For example, some of components in the embodiments are included in the present invention.

What is claimed is:

1. An endoscope comprising:
an image sensor disposed in a distal end portion in an insertion section to be inserted into a subject;
a first memory, which is a nonvolatile memory, disposed in the distal end portion and storing first information;
a controller disposed on a proximal end side relative to the distal end portion, electrically connected to the image sensor and the first memory, and communicable with the image sensor and the first memory; and
a second memory disposed on a proximal end side relative to the distal end portion, storing second information, and communicable with the controller,
wherein the controller
reads out the first information stored in the first memory and stores the first information as backup information in the second memory separately from the second information or as a part of the second information when the controller is started when supplied with power, and
reads out the first information stored in the second memory and transmits the read first information to a predetermined circuit when the controller receives a request from the circuit.

2. The endoscope according to claim 1, wherein the predetermined circuit is a processor device configured to supply predetermined power to the endoscope and enable predetermined information to be transmitted to and received from the endoscope when the endoscope is connected to the processor device, and
wherein the controller
reads out the first information stored in the first memory and stores the read first information as backup information in the second memory when the controller is started when supplied with power from the processor device, and
reads out the first information stored in the second memory and transmits the read first information to the processor device when the controller receives a request to transmit the first information from the processor device.

3. The endoscope according to claim 2, further comprising
a connector connected to the processor device, wherein the controller and the second memory are disposed in the connector.

4. The endoscope according to claim 3, wherein
the image sensor and the first memory are provided on a first substrate disposed in the distal end portion,
the controller and the second memory are provided on a second substrate disposed in the connector, the endoscope further comprising
a cable disposed in the insertion section and having one end connected to the first substrate, wherein
the second substrate is connected to the first substrate by being connected to a proximal end of the cable, and
the controller is electrically connected to the image sensor and the first memory via the cable, and is communicable with the image sensor and the first memory.

5. The endoscope according to claim 1, wherein
the image sensor and the first memory are provided on a first substrate disposed in the distal end portion, and
the controller and the second memory are provided on a second substrate disposed on a proximal end side relative to the distal end portion.

6. The endoscope according to claim 5, further comprising
an image sensor substrate that is disposed in the first substrate and on which the image sensor is mounted,
wherein the first memory is mounted as an IC package separate from the image sensor on the image sensor substrate.

7. The endoscope according to claim 5, further comprising
an image sensor substrate that is disposed in the first substrate and on which the image sensor is mounted,
wherein the first memory is stacked on the image sensor substrate and mounted on the substrate.

8. The endoscope according to claim 5, wherein
the first memory is provided in the image sensor.

9. The endoscope according to claim 1, wherein
the controller
includes a RAM (random access memory) connectable to the predetermined circuit, and
reads out the first information stored in the second memory and transmits the read first information to the predetermined circuit via the RAM when the controller receives a request to transmit the first information from the predetermined circuit, and
transmits the first information stored in the RAM to the predetermined circuit when the controller receives a same request again from the predetermined circuit.

10. The endoscope according to claim 1, wherein
the first information includes specific information about the image sensor.

11. The endoscope according to claim 1, wherein
the second information includes specific information about the endoscope, white balance, and other image processing information.

12. The endoscope according to claim 1, wherein
the second memory is a nonvolatile memory.

13. A method of operating an endoscope comprising
an image sensor disposed in a distal end portion in an insertion section to be inserted into a subject,
a first memory, which is a nonvolatile memory, disposed in the distal end portion and storing first information,
a controller disposed on a proximal end side relative to the distal end portion, electrically connected to the image sensor and the first memory, and communicable with the image sensor and the first memory, and
a second memory disposed on a proximal end side relative to the distal end portion, storing second information, and communicable with the controller,
the method comprising:
the controller reading out the first information stored in the first memory when the controller is started when supplied with power;
the controller storing the read first information as backup information in the second memory separately from the second information or as a part of the second information; and
the controller reading out the first information stored in the second memory and transmitting the read first information to a predetermined circuit when the controller receives a request from the circuit.

* * * * *